US012723027B2

(12) United States Patent
Smits et al.

(10) Patent No.: US 12,723,027 B2
(45) Date of Patent: Sep. 1, 2026

(54) PROCESS FOR THE PREPARATION OF 5-CHLORO-PYRIDINE- 2-CARBOXYLIC ACIDS AND CARBOXYLATES WITH 3-SULFUR CONTAINING SUBSTITUENTS

(71) Applicant: SYNGENTA CROP PROTECTION AG, Basel (CH)

(72) Inventors: Helmars Smits, Stein (CH); Mattia Riccardo Monaco, Stein (CH)

(73) Assignee: SYNGENTA CROP PROTECTION AG, Basel (CH)

( * ) Notice: Subject to any disclaimer, the term of this patent is extended or adjusted under 35 U.S.C. 154(b) by 943 days.

(21) Appl. No.: 17/779,854

(22) PCT Filed: Nov. 27, 2020

(86) PCT No.: PCT/EP2020/083696
§ 371 (c)(1),
(2) Date: May 25, 2022

(87) PCT Pub. No.: WO2021/105399
PCT Pub. Date: Jun. 3, 2021

(65) Prior Publication Data

US 2023/0025249 A1 Jan. 26, 2023

(30) Foreign Application Priority Data

Nov. 27, 2019 (EP) .................................... 19211678

(51) Int. Cl.
*C07D 213/803* (2006.01)
*C07D 213/79* (2006.01)

(52) U.S. Cl.
CPC ....... *C07D 213/803* (2013.01); *C07D 213/79* (2013.01)

(58) Field of Classification Search
CPC ................................................. C07D 213/803
USPC ......................................................... 546/314
See application file for complete search history.

(56) References Cited

U.S. PATENT DOCUMENTS

| | | | |
|---|---|---|---|
| 4,995,902 | A | 2/1991 | Brunner |
| 2018/0002345 | A1 | 1/2018 | Fischer et al. |

FOREIGN PATENT DOCUMENTS

| | | | |
|---|---|---|---|
| EP | 3 252 046 | A1 | 12/2017 |
| JP | H2-78662 | A | 3/1990 |
| WO | 2016005263 | A1 | 1/2016 |
| WO | 2016023954 | A2 | 2/2016 |
| WO | 2016046071 | A1 | 3/2016 |
| WO | 2016/071214 | A1 | 5/2016 |
| WO | 2016/087257 | A1 | 6/2016 |
| WO | 2016087265 | A1 | 6/2016 |

OTHER PUBLICATIONS

Written Opinion of the International Searching Authority and International Search Report for International Application No. PCT/EP2020/083696 mailed Jan. 25, 2021.

Extended European Search Report for Application No. EP 19211678.8, dated Mar. 11, 2020.

European Search Report issued in European Patent Application No. 20 811 643.4, mailed Nov. 28, 2023.

*Primary Examiner* — Kortney L. Klinkel
(74) *Attorney, Agent, or Firm* — BakerHostetler; Toni-Junell Herbert

(57) ABSTRACT

A process for the preparation of compound of formula I is provided: (I) where $R_1$ and $R_2$ are as defined in the description.

(I)

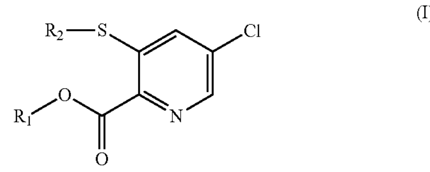

20 Claims, 1 Drawing Sheet

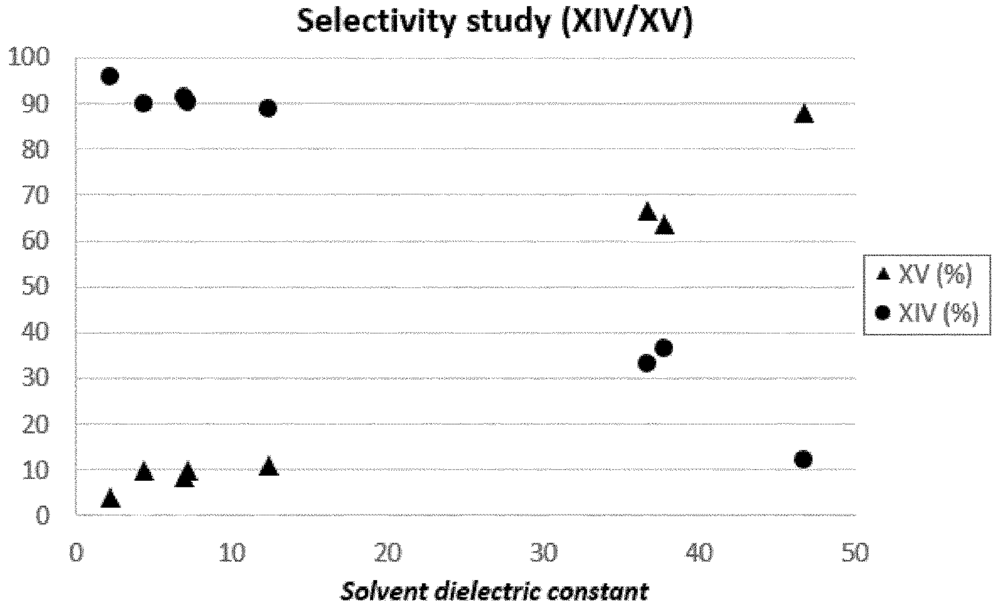
Selectivity study (XIV/XV)
100
90
80
70
60
50
40
30
20
10
0
0
10
20
30
40
50
Solvent dielectric constant
XV (%)
XIV (%)

PROCESS FOR THE PREPARATION OF 5-CHLORO-PYRIDINE- 2-CARBOXYLIC ACIDS AND CARBOXYLATES WITH 3-SULFUR CONTAINING SUBSTITUENTS

CROSS-REFERENCE TO RELATED APPLICATIONS

This application is a 371 National Stage application of International Application No. PCT/EP2020/083696 filed Nov. 27, 2020, which claims the benefit of EP 19211678.8, filed Nov. 27, 2019, the entire contents of these applications are hereby incorporated by reference.

The present invention relates to the preparation of 5-chloro pyridine-2-carboxylic acids and carboxylates with 3-sulfur containing substituents that are useful intermediates for the preparation of agrochemicals.

More particularly, the present invention relates to 5-chloro pyridine-2-carboxylic acids of formula I and to a process for preparation thereof (I)

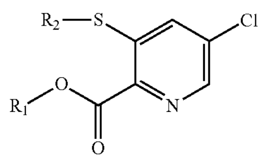

wherein $R_1$ is H or $C_1$-$C_4$alkyl; $R_2$ is $C_1$-$C_4$alkyl; or an agrochemically acceptable salt of a compound of formula (I).

5-halo-pyridine-2-carboxylic acids and carboxylates with 3-alkylsulfanyl substituents are useful intermediates for the preparation of biologically active compounds in the agrochemical industries as previously described, for example, in: WO 2016/005263, WO 2016/023954, WO 2016/030229, WO 2016/046071, WO 2016/059145, WO 2016/096584, WO 2016/104746 and WO 2019/065568.

Known synthesis of 5-halo-pyridine-2-carboxylic acids and carboxylates with 3-alkylsulfanyl substituents (Y) involve many reaction steps. For example, two routes to access the 5-bromo compounds (Y) have been reported (route A: CN105218437; route B: US2012/0165338 or *J. Org. Chem.* 2009, 74, 4547-4553) as shown in Scheme 1 ($R_1$ is $H_1$, $C_1$-$C_4$alkyl, or an alkali metal ion)

Scheme 1. Routes to 5-Br compounds (Y)

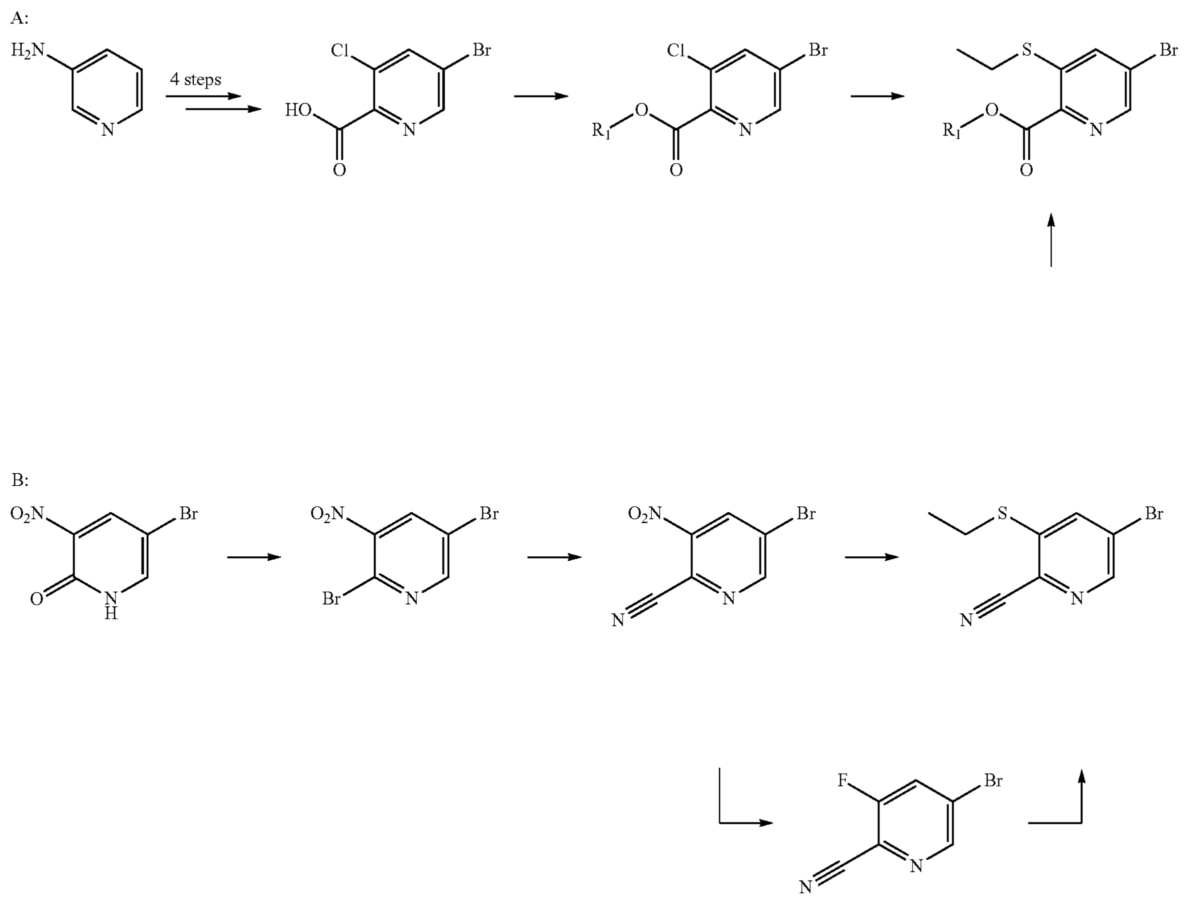

Access to the corresponding 5-iodo compounds (Y) has been reported in WO2016/104746 from commercially available 5,6-dichloronicotinic acid in seven steps, as shown in Scheme 2.

Scheme 2. 5-iodo compounds (Y)

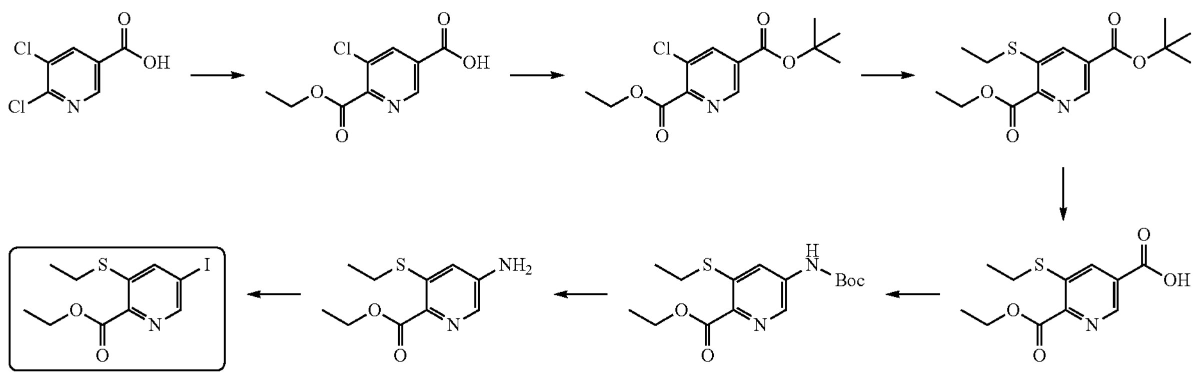

Clearly, such long and laborious syntheses are not suitable for preparing large amount of material due to low overall yields and large amount of waste generated. Therefore, it would be advantageous to have available a more efficient and more economical route to these intermediates.

Moreover, within the class of 5-halo-3-alkylsulfanyl-pyridine-2-carboxylic carboxylates, 5-chloro-3-alkylsulfanyl-pyridine-2-carboxylic acid and corresponding esters are undisclosed and a route for their preparation has been elusive. Due to the unavailability of chlorinated intermediates of formula (I), the synthetic community has been so far prompted to employ the bromo and iodo analogs for the preparation of biologically active agrochemicals (WO 2016/005263, WO 2016/096584, WO 2016/104746 WO 2016/023954, WO 2016/046071, WO 2016/087265, WO 2016/087257, WO 2016/030229, WO 2016/121997, WO 2016/104746). However, the use of building blocks of formula (I) in these syntheses would be greatly advantageous reducing the formation of bromine and iodine containing waste in following functionalization reactions at the 5-position (metal catalyzed cross coupling reactions, nucleophilic aromatic substitutions, etc) in favor of a more benign chlorine containing waste.

Moreover, compounds of formula (I) can be considered alternative convenient intermediates to significantly shorten the synthesis of other agrochemical products for which laborious and long routes were originally devised (WO 2019/065568, WO 2019/124529, WO 2020/050212).

Commercially available 3,5-dichloropyridine-2-carboxylic acid (VIII) and its corresponding esters (IX) wherein $R_1$ is $C_1$-$C_4$ alkyl could be convenient starting material for an intermediate of formula (VI) and (VII). In principle, all that would be required is a selective displacement of chlorine ortho to a carboxylate group with ethylthiolate (Scheme 3).

Scheme 3. Envisaged route to (VI) or (VII) from (VIII) or (IX)

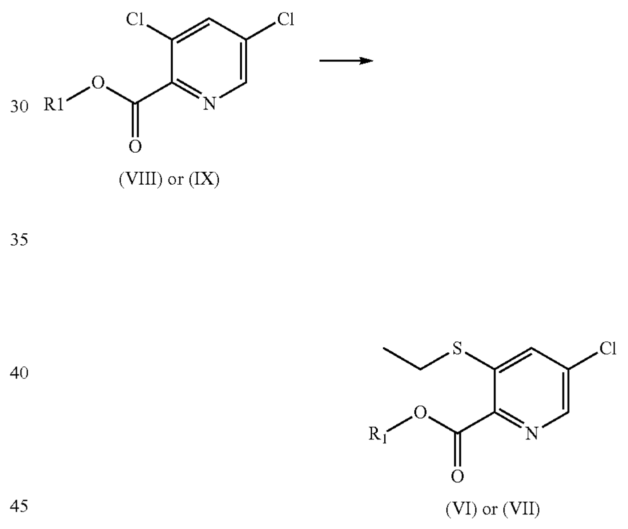

(VIII) or (IX)

(VI) or (VII)

However, it is not obvious that such a selectivity is achievable since the 2-carboxylate moiety renders the "ortho" position less sterically accessible and disfavors the formation of the desired 3-alkylsulfanyl product. In fact, reacting the compound of formula (IXa) under standard conditions for nucleophilic aromatic substitution reactions the undesired isomer (Xa) is preferentially obtained in all tested solvents (Scheme 4).

Scheme 4. Observed selectivity for reaction of (IXa)

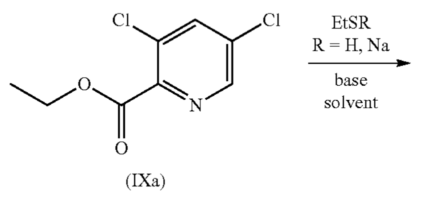

(IXa)

-continued

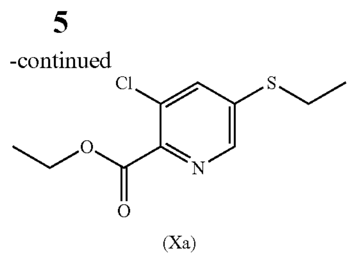

(Xa)

solvents: i.e. NMP, toluene ...

Ortho-selective thiolation reactions of polychlorinated aromatic compounds with a free acid moiety are challenging, rarely described, and are usually copper mediated via a carboxylate-directed Ullmann-type coupling (as for example described in Sambiagio C., Marsden S. P., Blacker A. J., McGowan P. C. *Chem. Soc. Rev.*, 2014, 43, 3525-3550) as shown in Scheme 5.

Scheme 5. Cu-mediated Ullmann-type coupling on chlorinated benzoic acid

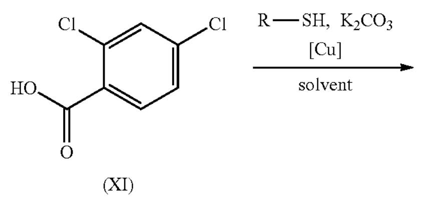

(XI)

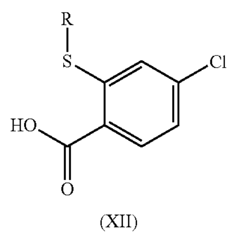

(XII)

No example of this reaction has ever been reported for polychlorinated picolinic acids.

Thus, according to the present invention, there is provided a process for the preparation of compound of formula I (scheme 6):

(I)

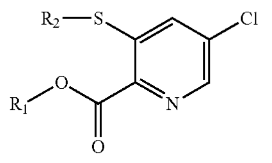

wherein $R_1$ is H or $C_1$-$C_4$alkyl; preferably $R_1$ is methyl, ethyl or t-butyl, more preferably Ri is ethyl; and $R_2$ is $C_1$-$C_4$alkyl; preferably $R_2$ is ethyl; which process comprises:

(A) reacting a compound of formula II (II)

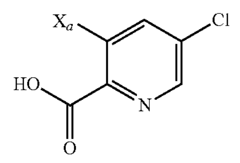

wherein Xa is fluoro or chloro; preferably Xa is chloro; with a thiol compound $R_3$—S—$R_2$ wherein $R_2$ is as defined in formula I and $R_3$ is H or an alkali metal ion; preferably $R_3$ is H, sodium, potassium or lithium, in the presence of a suitable base, in an appropriate solvent (or diluent) having a dielectric constant less than 15; to produce a compound of formula (Ia) or a salt thereof (Ia)

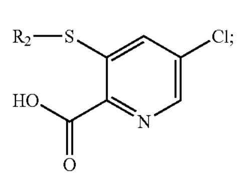

and, optionally, esterifying the compound of the formula (Ia) or a salt thereof in the presence of a compound of formula ROH, wherein R is $C_{1-4}$alkyl; to produce the compound of formula (I) where $R_1$ is $C_1$-$C_4$alkyl.

This process is demonstrated to be of great usefulness as it allows the synthesis of key building blocks for the preparation of agrochemicals in higher yields and with more favorable conditions with respect to previously described routes.

Compounds of formula I that are prepared by the inventive process that have at least one basic centre can form, for example, acid addition salts, for example with strong inorganic acids such as mineral acids, for example perchloric acid, sulfuric acid, nitric acid, nitrous acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium, lithium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

In each case, the compounds of formula (I) that are prepared by the process according to the invention are in free form or in salt form, e.g. an agronomically usable salt form.

The term "$C_1$-$C_4$alkyl" as used herein refers to a saturated straight-chain or branched hydrocarbon radical attached via any of the carbon atoms having 1 to 4 carbon atoms, for example, any one of the radicals methyl, ethyl, n-propyl, isopropyl, n-butyl, sec-butyl, isobutyl, t-butyl.

Surprisingly, it was found that in the absence of any copper catalyst high ortho selectivity for thiolation of 3,5-dichloropicolinic acid (a compound of formula (II) represented by the formula (VIII)) was observed in non-protic apolar solvents. In particular, it was found that the selectivity is remarkably influenced by the nature of the solvent: in solvents with high relative permittivity (i.e. DMSO [dielectric constant of 46.7]), high selectivity for the "para" isomer (XV) is observed, whereas in solvents with low relative permittivity (i.e. dioxane, toluene, 2-MeTHF . . . [dielectric constants of 2.25, 2.38, 6.97]), selective formation of "ortho" isomer (a compound of formula (Ia) represented by the formula (XIV)) is observed. This concept in shown in the Scheme 6.

Scheme 6. Observed selectivity for the thiolation of (VIII)

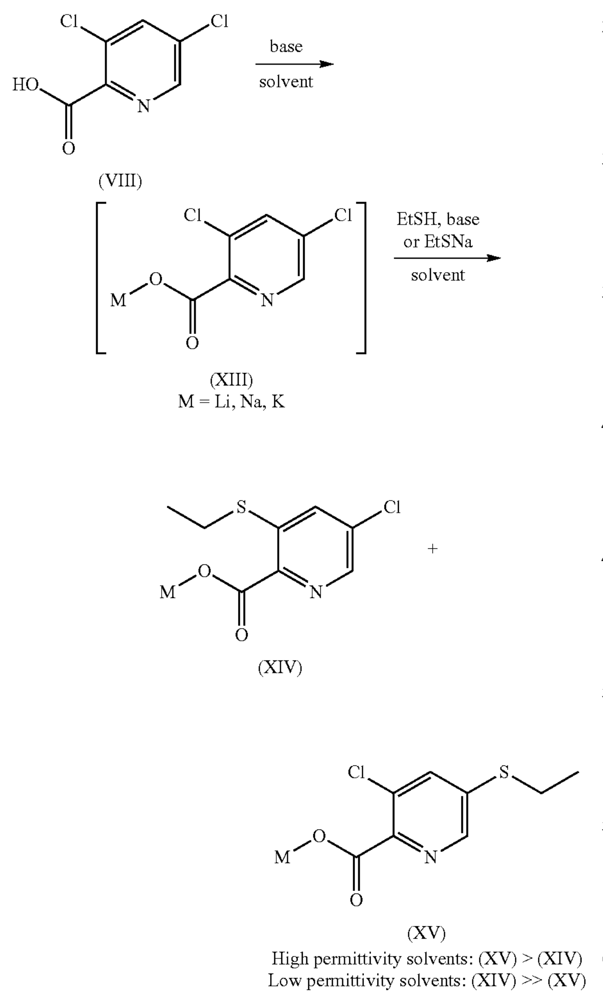

In another embodiment of the present invention, a compound of formula I represented by a compound of formula Ia, or an agrochemically acceptable salt of a compound of Ia, is provided:

(Ia)

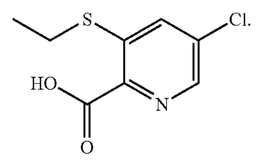

In further embodiment of the present invention, a compound of formula I represented by a compound of formula Ia-1 is provided:

(Ia-1)

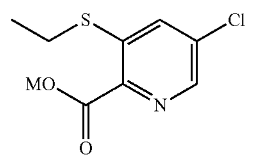

where M is sodium, potassium or lithium; preferably sodium or lithium.

In yet another embodiment of the present invention, a compound of formula I represented by a compound of formula 1-2, or an agrochemically acceptable salt of a compound of 1-2, is provided:

(I-2)

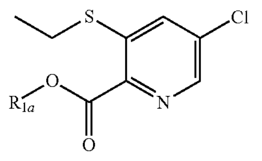

wherein $R_{1a}$ is $C_{1-4}$alkyl; preferably $R_{1a}$ is methyl, ethyl or t-butyl, more preferably $R_{1a}$ is ethyl.

In further embodiment of the present invention, a compound of formula 1-2a, or an agrochemically acceptable salt of a compound of 1-2a, is provided:

(I-2a)

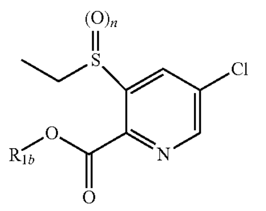

wherein $R_{1b}$ is $C_{1-4}$alkyl; preferably $R_{1b}$ is methyl, ethyl ort-butyl, more preferably $R_{1b}$ is ethyl; and n is 1 or 2; preferably n is 2.

Compounds of formula 1-2a can be prepared by oxidation of compounds of formula 1-2 by known methods such as those described in WO 2016/005263.

In the process according to the invention of making compounds of formula (I) (scheme 6), examples of suitable bases are alkali metal hydroxides or alkali metal carbonates. Examples which may be mentioned are sodium hydroxide, sodium carbonate, lithium hydroxide, potassium hydroxide, and potassium carbonate; preferably an alkali metal carbonate, more preferably sodium or potassium carbonate, most preferably potassium carbonate.

In the process according to the invention of making compounds of formula (I) (scheme 6), examples of appropriate solvents (or diluents) are those having a dielectric constant less than 15; more preferably, solvents (or diluents) having a dielectric constant less than 12; even more preferably, solvents (or diluents) having a dielectric constant less than 10. In another embodiment, the appropriate solvents (or diluents) have a dielectric constant less than 6. Examples of appropriate solvents (or diluents) are dioxane, methyltetrahydrofuran, toluene, anisole, pyridine; more preferably unpolar organic chosen from dioxane, methyltetrahydrofurane or toluene; most preferably appropriate solvents are those with a dielectric constant in the range from 1.5 to 15.

In one embodiment, in the process according to the invention of making compounds of formula (I) (scheme 6), the reaction is advantageously carried out in a temperature range from approximately 0° C. to approximately +140° C., preferably from approximately 0° C. to approximately +100° C., in many cases in the range between ambient temperature and approximately +80° C. In a preferred embodiment, the reaction of step a. is performed at temperatures between 0° C. and the boiling point of the reaction mixture, more preferably at temperatures between 20° C. and 100° C., most preferably in the temperature range of 60-100° C.

In one preferred embodiment, the present invention provides highly selective thiolation reactions of 3,5-dichloropicolinic acid compounds and the corresponding carboxylate salts of formula (II) wherein $R_1$ is as defined in formula I under scalable conditions using sodium ethanethiolate or ethanethiol and a base in a selected non-protic apolar solvent having a dielectric constant less than 15, producing alkyl 5-chloro-3-ethylsulfanyl-pyridine-2-carboxylate intermediates of formulae (Ia) and (Ib).

Ia (Ib)

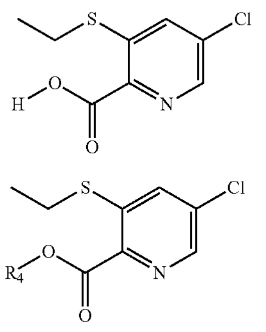

wherein $R_4$=$C_{1-4}$alkyl

BRIEF DESCRIPTION OF THE DRAWINGS

Having thus described the invention in general terms, reference will now be made to the accompanying drawing wherein: FIG. 1 is a diagram showing the observed selectivity in function of solvent dielectric constant. More specifically, FIG. 1 shows the correlation between the observed ortho-para-thiolation selectivity and the dielectric constant of the solvent in accordance with one embodiment of the invention.

This solvent-dependent phenomenon was further explored and a correlation between the observed selectivity and the dielectric constant of the solvent (Lide, D. R., ed. (2005) CRC *Handbook of Chemistry and Physics* ($86^{th}$ ed.). Boca Raton (FL): CRC Press. ISBN 0-8493-0486-5) was established as shown in FIG. 1.

PREPARATORY EXAMPLES

Throughout this description, LC/MS means Liquid Chromatography Mass Spectrometry and the following methods were used for the analysis of the compounds:

Method A: Spectra were recorded on a Mass Spectrometer from Waters (SQD, SQDII Single quadrupole mass spectrometer) equipped with an electrospray source (Polarity: positive and negative ions, Capillary: 3.00 kV, Cone range: 30 V, Extractor: 2.00 V, Source Temperature: 150° C., Desolvation Temperature: 350° C., Cone Gas Flow: 50 l/h, Desolvation Gas Flow: 650 l/h, Mass range: 100 to 900 Da) and an Acquity UPLC from Waters: Binary pump, heated column compartment, diode-array detector and ELSD detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH, gradient: 10-100% B in 1.2 min; Flow (ml/min) 0.85.

Method B: Spectra were recorded on a Mass Spectrometer from Waters (SQD Single quadrupole mass spectrometer) equipped with an electrospray source (Polarity: positive or negative ions, Full Scan, Capillary: 3.00 kV, Cone range: 41 V, Source Temperature: 150° C., Desolvation Temperature: 500° C., Cone Gas Flow: 50 L/Hr, Desolvation Gas Flow: 1000 L/Hr, Mass range: 110 to 800 Da) and a H-Class UPLC from Waters: Binary pump, heated column compartment and diode-array detector. Column:

Waters UPLC HSS T3 C18, 1.8 μm, 30×2.1 mm, Temp: 40° C., DAD Wavelength range (nm): 200 to 400, Solvent Gradient: A=water+5% Acetonitrile+0.1% HCOOH, B=Acetonitrile+0.05% HCOOH: gradient: 0 min 10% B; 0-0.2 min 10-50% B; 0.2-0.7 min 50-100% B; 0.7-1.3 min 100% B; 1.3-1.4 min 100-10% B; 1.4-1.6 min 10% B; Flow (mL/min) 0.6.

Example 1: Preparation of sodium;3,5-dichloropyridine-2-carboxylate (XIIIa)

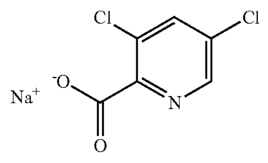

A mixture of 3,5-dichloropyridine-2-carboxylic acid (20.0 g, 104 mmol) and sodium hydroxide (1M in water, 100 mL, 100 mmol, 0.96 equiv.) was stirred at room temperature for 2 hours. The solution was filtered and the water was concentrated under reduced pressure to afford the desired product (94%, 22.0 g, 96.6 mmol, 93% yield) which was used without further purification.

$^1$H NMR (400 MHz, DMSO-d6) δ ppm 8.04 (d, J=2.20 Hz, 1H) 8.38 (d, J=2.20 Hz, 1H).

Example 2: Preparation of 5-chloro-3-ethylsulfanyl-pyridine-2-carboxylic acid (VI)

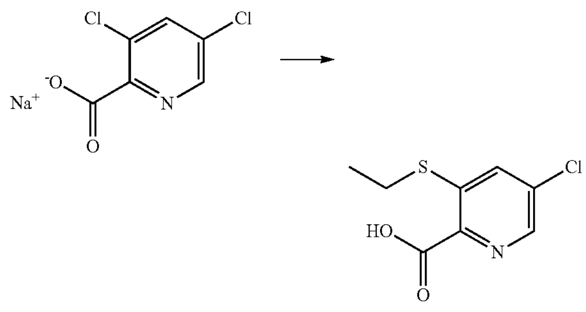

A round-bottomed flask was charged with sodium;3,5-dichloropyridine-2-carboxylate (94%, 4.00 g, 17.2 mmol). The flask was purged with argon and previously deoxygenated 2-methyltetrahydrofuran (86 mL) was added under argon. The reaction mixture was heated up to 70° C. and sodium ethanethiolate (1.82 g, 20.6 mmol, 1.19 equiv.) was added. It was then stirred at 70° C. for 7 hours. The reaction mixture was concentrated under reduced pressure. The resulting residue was dissolved in water (29 mL) and acetonitrile (12 mL). The insoluble particles were filtered off. The filtrate was heated up to 80° C. and additional water (10 mL) and acetonitrile (5 mL) were added. At 80° C., hot 1N hydrochloric acid (45° C., 16 mL) was added dropwise and it was kept stirring for few minutes. The obtained prepicitate was filtered hot and dried under reduced pressure to afford the desired product (94%, 2.30 g, 9.95 mmol, 58% yield).

LC-MS (method A): retention time 0.77 min, m/z 218 $[M+H^+]$.

$^1H$ NMR (400 MHz, DMSO-d6) δ ppm 1.25 (t, J=7.34 Hz, 3H) 3.02 (q, J=7.34 Hz, 2H) 7.93 (d, J=1.83 Hz, 1H) 8.41 (d, J=1.83 Hz, 1H).

Example 3: Preparation of 5-chloro-3-ethylsulfanyl-pyridine-2-carboxylic acid (VI)

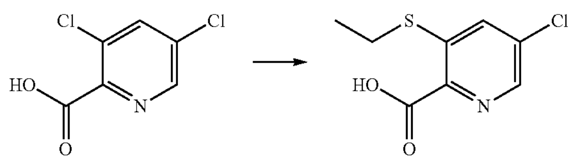

To a stirred solution of 3,5-dichloropyridine-2-carboxylic acid (1.00 g, 5.21 mmol) and sodium carbonate (0.662 g, 6.25 mmol, 1.20 equiv.) in previously deoxygenated 2-methyltetrahydrofuran (13 mL) was added at room temperature sodium ethanethiolate (0.920 g, 10.9 mmol, 2.10 equiv.). The reaction mixture was heated up to 50° C. and stirred for 3 hours. Additional 2-methyltetrahydrofuran (13 mL) was added and the reaction mixture was stirred at 50° C. for 18 hours. After cooling down to room temperature, the reaction mixture was diluted with water and 2-methyltetrahydrofuran was removed in vacuo. Acetonitrile (6 mL) was added, followed by dropwise addition of 1N hydrochloric acid (21 mL). The resulting precipitate was filtered and dried under reduced pressure to afford the desired product (71%, 1.00 g, 3.27 mmol, 63% yield).

Example 4: Preparation of 3-chloro-5-ethylsulfanyl-pyridine-2-carboxylic acid (XVI)

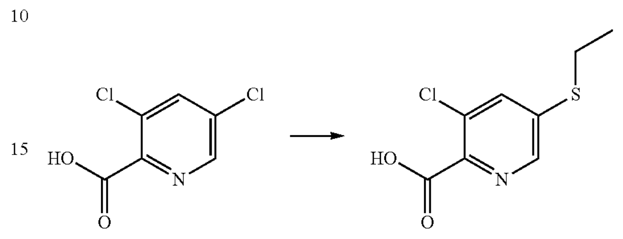

A solution of 3,5-dichloropyridine-2-carboxylic acid (0.500 g, 2.47 mmol) in dimethylsulfoxide (5.5 mL) was prepared and heated up to 100° C. Potassium carbonate (0.378 g, 2.60 mmol, 1.05 equiv.) was added and the reaction mixture was stirred at 100° C. for 1 hour. Sodium ethanethiolate (0.250 g, 2.97 mmol, 1.20 equiv.) was then added and the reaction mixture was kept stirring at 100° C. overnight. After cooling down to room temperature, the reaction mixture was diluted with ethyl acetate and water. The aqueous layer was then acidified and extracted with more ethyl acetate. The combined organic layers were washed with brine, dried over sodium sulfate, filtered and concentrated under reduced pressure. Purification of the crude material by reverse-phase chromatography afforded the desired product as a white solid (0.536 mmol, 22% yield).

LC-MS (method A): retention time 0.74 min, m/z 218 $[M+H^+]$.

$^1H$ NMR (400 MHz, DMSO-d6) δ ppm 1.26 (t, J=7.15 Hz, 3H) 3.10-3.18 (q, J=7.15 Hz, 2H) 7.95 (d, J=2.20 Hz, 1H) 8.44 (s, 1H).

Example 5: Preparation of ethyl 5-chloro-3-ethylsulfanyl-pyridine-2-carboxylate

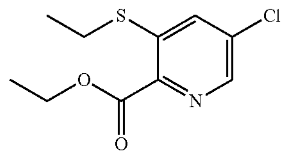

To a suspension of 5-chloro-3-ethylsulfanyl-pyridine-2-carboxylic acid (2.35 g, 10.6 mmol) in ethanol (26 mL) was added slowly at room temperature sulfuric acid (0.575 mL, 10.6 mmol, 1.00 equiv.). The reaction mixture was heated up to 70° C. and stirred for 15 hours. After cooling down to room temperature, the reaction mixture was concentrated under reduced pressure. The obtained residue was diluted in ethyl acetate, washed twice with sodium bicarbonate sat. aq., dried over sodium sulfate, filtered and concentrated under reduced pressure to afford the desired product (90%, 2.55 g, 9.34 mmol, 88% yield) which was used without further purification.

LC-MS (method A): retention time 0.99 min, m/z 246 $[M+H^+]$.

$^1$H NMR (400 MHz, chloroform-d) δ ppm 1.39-1.47 (m, 6H) 2.93 (q, J=7.34 Hz, 2H) 4.48 (q, J=7.21 Hz, 2H) 7.62 (d, J=2.20 Hz, 1H) 8.37 (d, J=1.83 Hz, 1H).

Example 6: Preparation of ethyl 3-chloro-5-ethylsulfanyl-pyridine-2-carboxylate (VIIa)

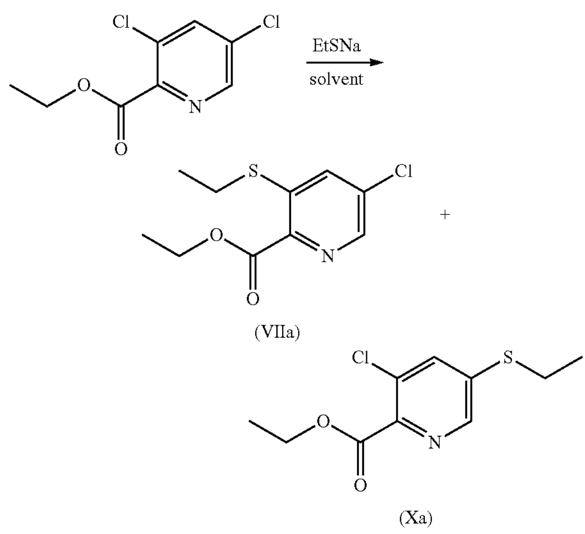

(VIIa)

+

(Xa)

To a stirred solution of ethyl 3,5-dichloropyridine-2-carboxylate (96%, 0.200 g, 0.873 mmol) in toluene (2 mL) was added at 0° C. sodium ethanethiolate (0.122 g, 1.31 mmol, 1.50 equiv.). The reaction mixture was allowed to reach room temperature and was stirred first at this temperature for 24 hours, and then for 15 hours at 80° C. After cooling down to room temperature, a LC-MS sample was measured to determine the ratio of the formed products VIIa and Xa. The results gave 60% conversion of starting material and the formation of VIIa:Xa with a ratio of 1:1.9.

LC-MS (method B): retention time 1.08 min, m/z 246 [M+H$^+$].

$^1$H NMR (400 MHz, chloroform-d) δ ppm 1.36-1.47 (m, 6H) 3.04 (q, J=7.42 Hz, 2H) 4.47 (q, J=7.09 Hz, 2H) 7.62 (d, J=2.08 Hz, 1H) 8.42 (d, J=1.96 Hz, 1H).

Example 7: Preparation of ethyl 3-chloro-5-ethylsulfanyl-pyridine-2-carboxylate (VIIa)

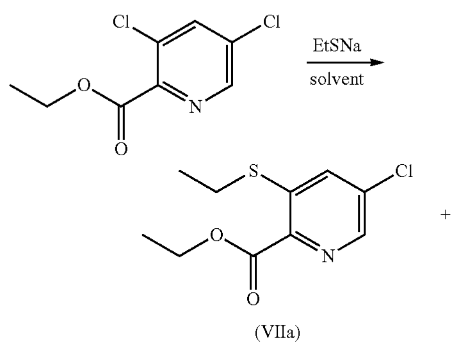

+

(VIIa)

-continued

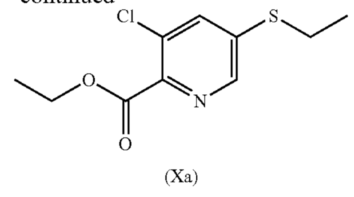

(Xa)

To a stirred solution of ethyl 3,5-dichloropyridine-2-carboxylate (95%, 0.200 g, 0.863 mmol) in 1-methyl-2-pyrrolidinone (2 mL) was added at 0° C. sodium ethanethiolate (0.099 g, 1.04 mmol, 1.20 equiv.). The reaction mixture was allowed to reach room temperature and was stirred for 6 hours. A LC-MS sample was measured to determine the ratio of the formed products VIIa and Xa. The results gave 70% conversion of starting material and the formation of VIIa:Xa with a ratio of 1:10.2.

LC-MS (method B): retention time 1.08 min, m/z 246 [M+H$^+$].

$^1$H NMR (400 MHz, chloroform-d) δ ppm 1.36-1.47 (m, 6H) 3.04 (q, J=7.42 Hz, 2H) 4.47 (q, J=7.09 Hz, 2H) 7.62 (d, J=2.08 Hz, 1H) 8.42 (d, J=1.96 Hz, 1H).

Example 8: Solvent Effect on the Thiolation Reaction on Sodium 3,5-dichloropyridine-2-carboxylate (XIIIa)

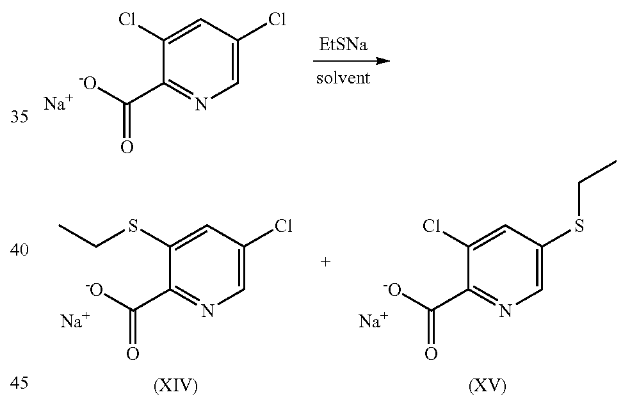

+

(XIV) (XV)

A 5 mL microwave vial was charged with sodium;3,5-dichloropyridine-2-carboxylate (94%, 100 mg, 0.422 mmol). The vial was purged with argon and previously deoxygenated solvent (2.2 mL) was added under argon. The reaction mixture was heated up to 80° C. and sodium; ethanethiolate (42.6 mg, 0,507 mmol, 1.20 equiv.) was added. The reaction mixture was stirred for 3.5 hours at 80° C. After cooling down to room temperature, the reaction mixture was stopped and a NMR sample was measured to determine the ratio of the formed products (XIV) and (XV). The results are summarized in the table below.

| Entry | Solvent | Dielectric constant | Conversion (%) | XV (%) | XIV (%) |
|---|---|---|---|---|---|
| 1 | DMSO | 46.7 | 99 | 88 | 12 |
| 2 | DMA | 37.8 | 87 | 64 | 36 |
| 3 | DMF | 36.7 | 82 | 67 | 33 |
| 4 | Pyridine | 12.4 | 87 | 11 | 89 |
| 5 | Dimethoxyethane | 7.2 | 82 | 10 | 90 |

-continued

| Entry | Solvent | Dielectric constant | Conversion (%) | XV (%) | XIV (%) |
|---|---|---|---|---|---|
| 6 | 2-MeTHF | 6.97 | 93 | 9 | 91 |
| 7 | Anisole | 4.33 | 76 | 10 | 90 |
| 8 | Dioxane | 2.25 | 93 | 4 | 96 |

The invention claimed is:

1. A process for the preparation of a chloro-pyridine compound of formula (I):

(I)

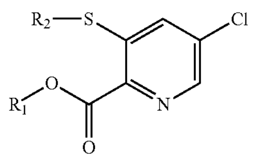

wherein $R_1$ is H or $C_1$-$C_4$alkyl; and
$R_2$ is $C_1$-$C_4$alkyl;
said process comprising:
(A) reacting a compound of formula II (II)

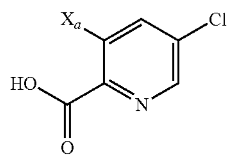

wherein Xa is fluoro or chloro,
with a thiol compound $R_3$—S—$R_2$, wherein $R_2$ is as defined in formula I and $R_3$ is H or an alkali metal ion; in the presence of a base and a solvent or a diluent having a dielectric constant less than 15 to produce a compound of formula (Ia) or a salt thereof (Ia)

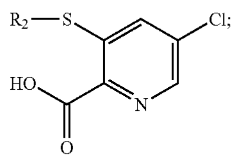

and,
optionally, esterifying the compound of the formula (Ia) or a salt thereof in the presence of a compound of formula ROH, wherein R is $C_{1-4}$alkyl to produce the compound of formula (I) where $R_1$ is $C_1$-$C_4$alkyl.

2. The process according to claim 1, wherein
Xa is chloro;
$R_1$ is ethyl;
$R_2$ is ethyl; and
$R_3$ is sodium.

3. The process according to claim 1, wherein the base comprises sodium hydroxide, sodium carbonate, or potassium carbonate.

4. The process according to claim 1, wherein the dielectric constant is in the range of 1.5 to 15.

5. The process according to claim 4, wherein the solvent or the diluent is selected from the group consisting of dioxane, methyltetrahydrofuran, toluene, anisole, pyridine.

6. The process according to claim 1, wherein the reaction of step (A) is performed at temperatures between 0° C. and the boiling point of the reaction mixture.

7. The process according to claim 1,
wherein
Xa in the formula (II) is chloro; or
$R_3$ in the thiol compound $R_3$—S—$R_2$ is H or sodium.

8. The process according to claim 1, wherein the base is potassium carbonate.

9. The process according to claim 1, wherein the temperature is between about 50° C. to about 100° C.

10. The process according to claim 1, wherein the solvent is selected from the group consisting of dioxane, methyltetrahydrofuran, and toluene.

11. The process according to claim 1, wherein the solvent is a non-protic apolar solvent.

12. The process according to claim 1, wherein the process is absence of any copper catalyst.

13. A compound of formula Ia, or an agrochemically acceptable salt of the compound of Ia:

(Ia)

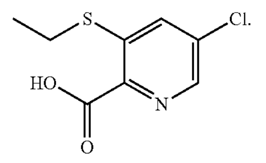

14. A compound of formula Ia-1:

(Ia-1)

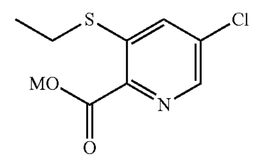

wherein M is sodium, potassium or lithium.

15. The compound of formula Ia-1 according to claim 14, wherein M is sodium or lithium.

16. A compound of formula I-2, or an agrochemically acceptable salt of the compound of I-2:

(I-2)

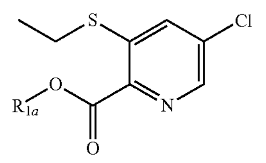

wherein $R_{1a}$ is $C_{1-4}$alkyl.

17. The compound of formula I-2 according to claim 16, wherein $R_{1a}$ is methyl, ethyl, or t-butyl.

18. A compound of formula I-2a, or an agrochemically acceptable salt of the compound of I-2a:

(I-2a)
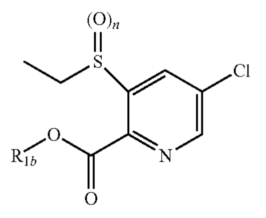
wherein $R_{1b}$ is $C_{1-4}$alkyl; and
n is 1 or 2.
19. The compound of formula I-2a according to claim 18, wherein $R_{1b}$ is methyl, ethyl or t-butyl; or n is 2.
20. The compound of formula I-2a according to claim 18, wherein $R_{1b}$ is ethyl, and n is 2.
* * * * *